United States Patent [19]

Colin et al.

[11] 4,111,554

[45] Sep. 5, 1978

[54] PROCESS FOR THE SPECIFIC QUANTITATIVE DETECTION OF SULFUR COMPOUNDS AND APPARATUS FOR CARRYING OUT THIS PROCESS

[75] Inventors: Jean-Michel Colin; Dominique Herouard, both of Le Havre, France

[73] Assignee: Compagnie Francaise de Raffinage, Paris, France

[21] Appl. No.: 658,506

[22] Filed: Feb. 17, 1976

[30] Foreign Application Priority Data

Feb. 18, 1975 [FR] France .................... 75 05048

[51] Int. Cl.² .................... G01N 1/00; G01N 21/58
[52] U.S. Cl. .................... 356/36; 73/23.1; 356/72; 356/187
[58] Field of Search .................... 356/36, 72, 87, 187, 356/96; 73/23.1; 23/254 EF

[56] References Cited

U.S. PATENT DOCUMENTS

| | | | |
|---|---|---|---|
| 3,489,498 | 1/1970 | Brody et al. | 356/72 |
| 3,499,160 | 3/1970 | Gordon | 356/96 |
| 3,556,730 | 1/1971 | Mitacet | 73/23.1 |
| 3,582,659 | 6/1971 | Dekker | 356/96 |
| 3,877,819 | 4/1975 | Haas | 356/187 |
| 3,967,931 | 7/1976 | Juvet, Jr. et al. | 23/254 EF |

FOREIGN PATENT DOCUMENTS

1,207,671 0000 United Kingdom.

Primary Examiner—Vincent P. McGraw
Attorney, Agent, or Firm—Curtis, Morris & Safford

[57] ABSTRACT

An improved flame photometry detector to give direct quantitative detection of molecules containing sulfur by:

— the total combustion of the mixture to be analyzed so as to transform the sulfur into sulfur oxide (primarily $SO_2$);

— the linearization, by an electronic device, of the signal supplied by the electrometer, in series with the photomultiplier of the detector, prior to recording (this results in the proportionality of the recording to the number of sulfur-containing molecules detected); and preferably the provision of a leakage flow beyond the burner and in front of the detection so as to avoid saturation of the detector.

These improvements can be applied to the analysis of a hydrocarbon mixture and of sulfur compounds which have been previously eluted on a chromatographic column.

15 Claims, 5 Drawing Figures

PROCESS FOR THE SPECIFIC QUANTITATIVE DETECTION OF SULFUR COMPOUNDS AND APPARATUS FOR CARRYING OUT THIS PROCESS

The present invention concerns the specific quantitative detection of sulfur compounds by flame photometry. More particularly it concerns an improvement which makes it possible to improve the response supplied by a flame-photometry detector and to utilize the response with precision on a quantitative plane.

It is known that the flame photometry detector can be used either directly or downstream of a gaseous phase chormatograhic separation column for the specific detection of chemical species such as molecules which contain sulfur atoms. The principle of this detector is the amplification, by a photomultiplier, of the light emitted at a given wavelength by the meta-stable species $S_2$ formed by decomposition of the substances containing sulfur atoms in a highly reductive flame whose temperature is close to 400° C.

In its reduction to practice, this detector generally consists of a tube for the introduction of the effluent to be analyzed, into which tube there discharges a tube for the feeding of a combustion-supporting gas (air or oxygen) which is necessary for the flame of the detector. This mixture is introduced into a burner which is furthermore fed with an excess of hydrogen (generally introduced annularly). The wavelength is selected by a removable monochromatic filter, which is generally protected from the effects of the flame by a heat filter.

The monochromatic filter generally employed for the detection of the element sulfur is selective for the value of 394 millimicrons.

This type of detector is extensively used, particularly in the chemical industry and in the petroleum industry since it possesses great specificity for the detection of sulfur in the hydrocarbon compounds.

However, it has a certain number of drawbacks which are, in particular:
— the non-linearity (proportionality) of the height of the peaks as a function of the number of sulfur-containing molecules (the height of the peaks is as a matter of fact proportional to the mass of sulfur raised to a certain power);
— the influence of the nature of the sulfur compound on the response (the value of the power mentioned above varies from one sulfur compound to another; by way of example, it is equal to 1.69 for sulfur in the form of $SO_2$ and to 1.76 for sulfur in the form of $SH_2$);
— the influence of the total quantity of compounds (sulfur compounds and other compounds such as hydrocarbons) introduced into the detector on the specific response of said detector, this defect being probably due to saturation of the detector.

These drawbacks make a quantitative determination of the sulfur compounds practically impossible.

Furthermore, the flame photometry detector when it is placed downstream of a chromatographic separation column is generally used with another non-specific detector (for instance a flame ionization detector), intended to provide a qualitative analysis of the entire components of the sample in which the sulfur compounds are contained. This is the reason why the flame photometry detectors sold on the market contain a flame ionization detector in the same housing; the flame is common to both detectors. However, the results which are obtained by causing the two detectors to operate simultaneously are not satisfactory since while the flame photometry detector requires a reductive flame in order to operate satisfactorily, the flame ionization detector on its part requires an oxidizing flame.

More generally, the conventional detectors such as flame ionization detectors cannot provide a complete quantitative analysis of a sample containing compounds having sulfur atoms since interferences occur between the peaks representing the sulfur compounds and the peaks representing the other compounds (for example hydrocarbon compounds). These interferences do not permit a precise determination of the respective area of the peaks.

An object of the present invention is to improve the specific detection of the sulfur compounds by means of a flame photometry detector and in particular to permit the quantitative determination of these compounds.

A preferred embodiment of the present invention is a process for the specific detection of sulfur compounds by means of a flame photometry detector, this process being characterized by the fact that:
— on the one hand, prior to the introduction of the mixture into the detector the mixture is subjected to a complete combustion intended to convert all of the sulfur compounds into sulfur oxides, whereupon an adjustable fraction of the effluent of the combustion is introduced into the flame photometry detector;
— on the other hand, the signal supplied by the electrometer in series with the photomultiplier of the flame photometry detector is previously linearized, that is to say made proportional to the number of sulfur molecules detected before it is recorded.

Another preferred embodiment of the invention consists of a device for the detection of sulfur compounds consisting in series of a flame photometry detector provided with a photomultiplier, of an electrometer, and of a recorder; said device being characterized by the fact that it also comprises:
— a burner placed within an enclosure for the complete combustion of the sample, said enclosure being located upstream of the flame photometry detector;
— a device placed on a bypass so as to cause a loss of head and thus adjust the leakage flow of the effluent from the combustion enclosure, said bypass being located between the complete combustion enclosure and the flame photometry detector;
— a device, placed in series between the electrometer and the recorder, to convert the output voltage of the electrometer into a voltage which is proportional to the number of sulfur molecules detected.

Another preferred embodiment of the invention is the application of the process described above to the specific detection of the sulfur compounds contained in a sample which contains also other compounds — for example hydrocarbon compounds. This application is characterized by the fact that the sample is separated into its components by chromatographic means whereupon the components are treated by the process described above as they are eluted.

The devices for carrying out the process described above also form embodiments of the present invention.

The applicants have conceived of overcoming the influence of the nature of the sulfur compound on the response of the flame photometry detector by causing the complete combustion of the gaseous mixture whose content of sulfur compounds it is desired to determine. The combustion is effected by means of a burner which is placed in an enclosure located upstream of the flame photometry detector. The burner is fed with hydrogen and oxygen, pure or diluted (air for instance can be used). The sample to be analyzed is introduced upstream of the burner into a stream of carrier gas which is not reactive under the conditions of the analysis (for example, argon).

The amount of oxygen present must be in excess. The sulfur present is transformed completely into oxides of sulfur. Sulfur dioxide is obtained practically exclusively, but sulfur trioxide is also formed. This does not constitute a drawback since sulfur dioxide and sulfur trioxide supply a single signal with the flame photometry detector.

The carbon and the hydrogen present in the medium subjected to the complete combustion are transformed into carbon dioxide and water respectively.

In accordance with the invention only a part of the gaseous mixture resulting from the complete combustion is introduced into the flame photometry detector. An adjustable leak is as a matter of fact placed between the combustion furnace and the detector. The presence of this leak makes it possible to avoid saturation of the detector, which has been mentioned above as a drawback.

The applicants have also devised an electronic device which is intended to be placed between the electrometer and the recorder. It is known that in the conventional circuit the electrometer is the device which receives the photomultiplier an electrical signal which is proportional to the luminous intensity transmitted by the monochromator filter and transforms it into an input signal — which is a voltage — for the recorder.

The electronic device in accordance with the invention transforms the voltage supplied by the electrometer into a voltage proportional to the mass of sulfur detected. Stated differently, the device "linearizes" the voltage supplied by the electrometer.

In this specification and the accompanying drawings we have shown and described a preferred embodiment of our invention and have suggested various alternatives and modifications thereof; but it is to be understood that these are not intended to be exhaustive and that many other changes and modifications can be made within the scope of the invention. These suggestions herein are selected and included for purposes of illustration in order that others skilled in the art will more fully understand the invention and the principles thereof and will thus be enabled to modify it and embody it in a variety of forms, each as may be best suited to the conditions of a particular use.

In the accompanying drawings.

In these various figures, the same reference numbers designate the same parts.

Figure 1:
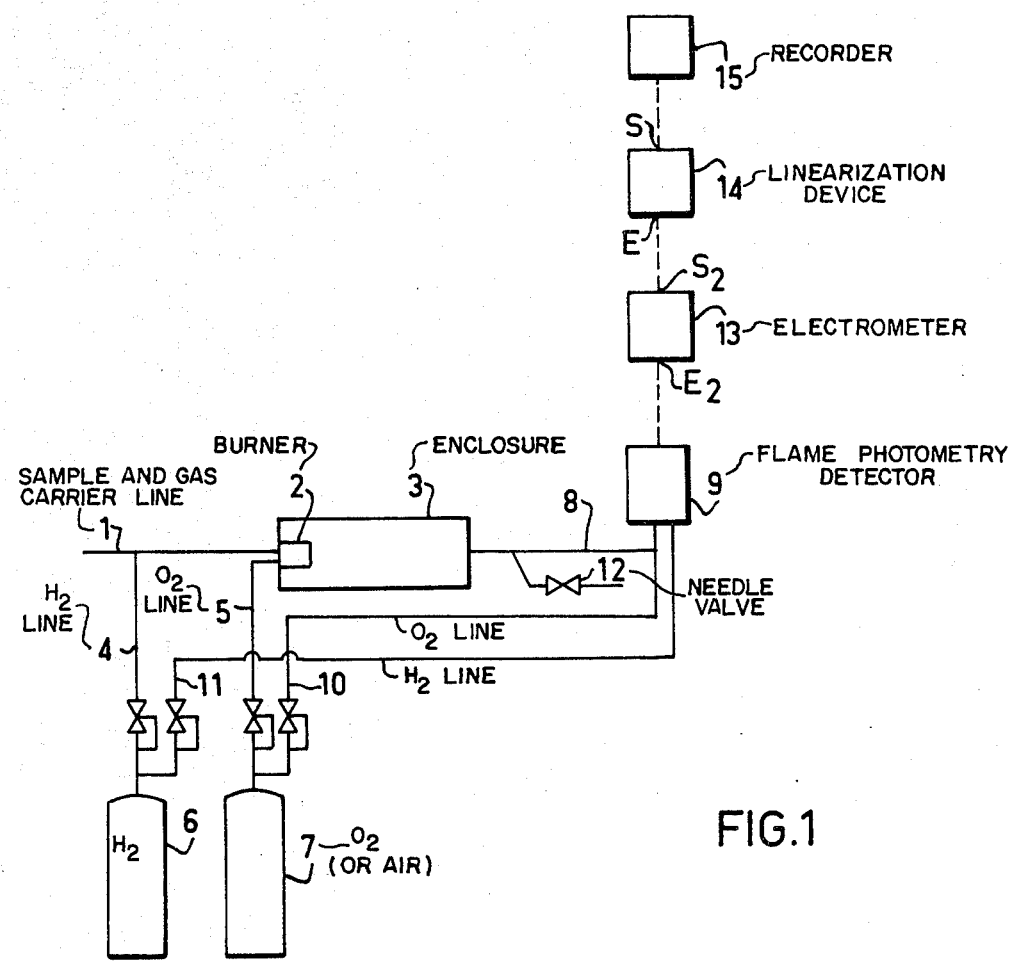
FIG. 1 is a general diagram of the component parts of the invention.
Figure 2:
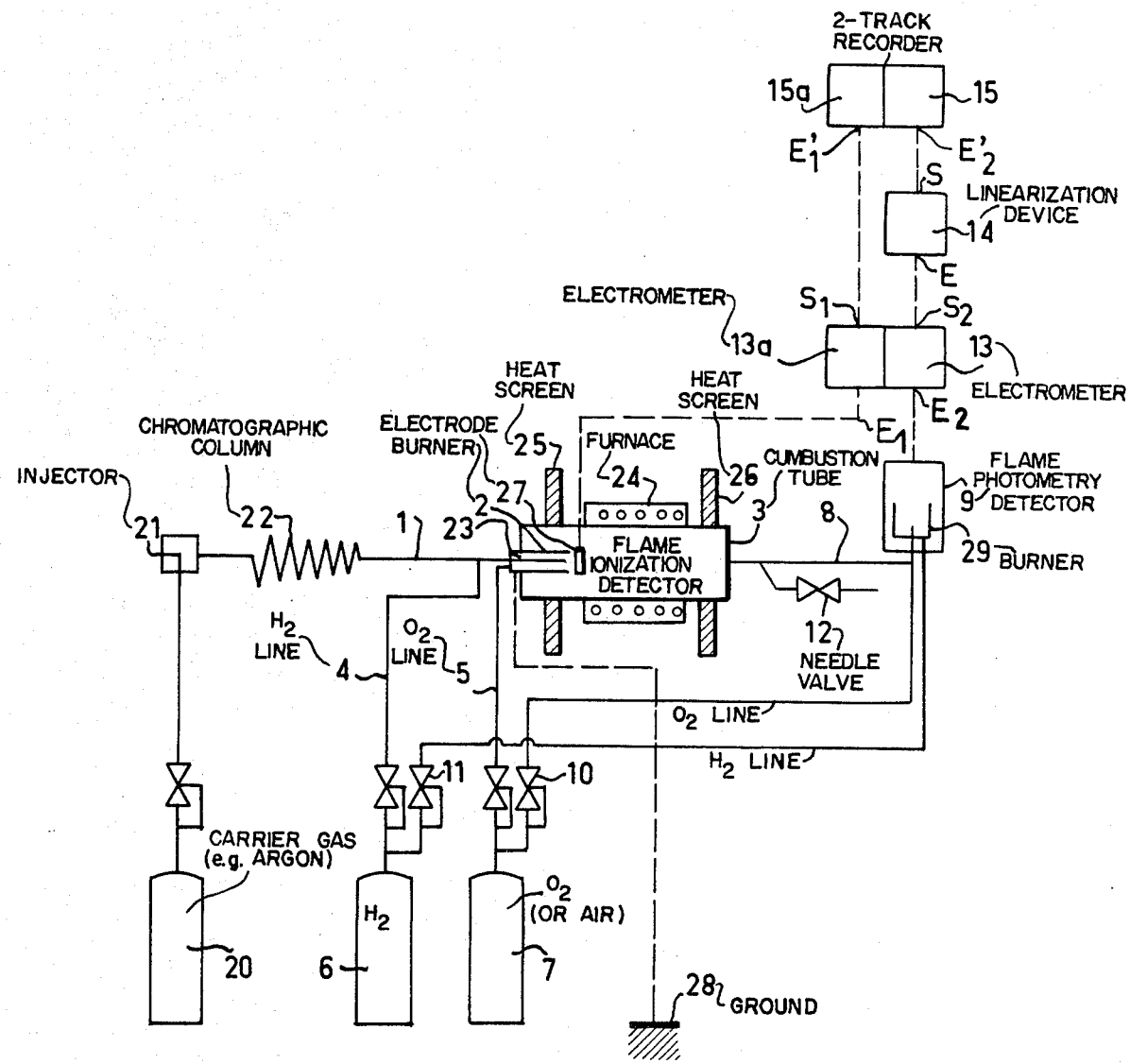
FIG. 2 is a diagram of a device which utilizes the invention in combination with a chromatographic separation column.

In FIGS. 1 and 2, the solid connecting lines designate pneumatic connections; the dash lines designate electrical connections.

Refer first of all to FIG. 1.

The sample of gas, in which it is desired to determine the amount of the element sulfur mixed with an inert carrier gas, is introduced via the line 1 into a burner 2 located within an enclosure 3. The hydrogen and the oxygen (pure or diluted) necessary for the complete combustion are introduced by the lines 4 and 5 respectively from the containers 6 and 7 respectively. A fraction of the efflux of the complete combustion passes via the line 8 into a flame photometry detector 9, which latter is known in the art. The burner (not shown) of the flame photometry detector 9 is fed with pure or dilute oxygen (for instance air) and hydrogen via the lines 10 and 11 respectively. 12 designates a needle valve intended inter alia to create a loss in head, and which permits adjustments of the leakage flow of the efflux from the complete combustion enclosure 3. The output signal of the photomultiplier (not shown) which the detector 9 contains is introduced into an electrometer 13 which produces a signal for the linearization device 14 described with reference to FIG. 3. The output signal of the device 14 is introduced into the recorder 15 which furnishes a signal whose amplitude is proportional to the mass of sulfur contained in the sample. The line 1 contains means for injection into the carrier gas which have not been shown.

When the flame photometry detector is used in combination with a prior chromatographic separation of the components of the sample — of which it is desired to determine the content of compounds having sulfur atoms — the device for the carrying out of the process of the invention is then preferably the one shown in FIG. 2, to which reference will now be had.

The sample is introduced in gaseous or liquid state into a stream of carrier gas (argon, for instance, coming from the container 20) via the injector 21. When the sample is in liquid state, it must be vaporized before entering the chromatographic column 22. This column must be adapted to the sample from which it is desired to remove the components. It does not constitute an object of the invention. As it is eluted, the efflux of the column 22 arrives, mixed with hydrogen stored in the container 6, into the central portion of a burner 2 located at the entrance to the combustion tube 3, which is for instance made of quartz. The hydrogen is introduced continuously into the stream of carrier gas. Pure or dilute oxygen coming from the container 7 is injected continuously through the annular space 23. The tube 3 is placed, at least over a fraction of its length, within a furnace 24. The function of the furnace 24 is twofold: on the one hand it makes it possible to effect the ignition of the hydrogen in the burner 2 and, on the other hand, it makes it possible to increase the temperature of the gaseous mixture downstream of the burner in order to avoid condensation of the water vapor. The walls 25 and 26 constitute heat screens which can be made of asbestos. Within the tube 3 there is also provided a flame ionization detector, whose flame is specifically that of the burner 2. This detector furthermore comprises a measuring electrode 27 and a counter electrode, which is the burner 2. The measuring electrode is connected to the input $E_1$ of an electrometer 13a. The counter electrode is connected to ground, 28.

A fraction — which can be adjusted by means of the needle valve 12 — of the efflux of the tube 3, is introduced together with oxygen coming from the container 7, into the flame photometry detector 9, known in the art (of which there has been shown only the burner 29) — and that very diagrammatically — which gives rise to the flame. The oxygen is introduced continuously.

The hydrogen coming from the container 6 is introduced continuously through an annular space at the periphery of the burner 2. The filters and the photomultiplier of the detector 9 have not been shown. The signal produced by the photomultiplier is received by the electrometer 13 at its input $E_2$.

The electrometer is a double electrometer. It has two inputs $E_1$ and $E_2$ for the flame ionization detector and for the flame photometry detector respectively. The double electrometer 13a-13 produces two signals at the outputs $S_1$ and $S_2$. The signal emitted by $S_1$ (which corresponds to the input $E_1$) is sent to the input $E_1'$ of the double track recorder 15a-15. The signal emitted by $S_2$ (which corresponds to the input $E_2$) is sent to the input E of the linearization device 14 described below with reference to FIG. 3. The signal emitted by the output S of the device 14 is sent to the input $E_2'$ of the double recorder 15a-15. This double recorder furnishes two recordings simultaneously. The first recording — from the input signal $E_1'$ — consists of the complete chromatographic analysis of the sample. The second recording — from the input signal $E_2'$ — has an amplitude which is proportional to the amount of sulfur contained in the combustion gases coming from the enclosure 3.

In FIG. 2 a flame ionization detector has been shown. However, the function of this detector could be provided by a non-descructive detector (for example a catharometer detector), placed in series with the column 22.

The combination of the two detectors, as described with reference to FIG. 2, makes it possible to note simultaneously during their elution, on the one hand the recording of the qualitative analysis and possibly of the quantitative analysis of the compounds of the sample, provided by the flame ionization detector (except with reference to the sulfur compounds whose quantitative analysis is generally not possible due to interferences between the peaks of the sulfur compounds and the other peaks) and, on the other hand, the recording of the specific quantitative analysis of the sulfur compounds of the sample, provided by the flame photometry detector.

Figure 3:
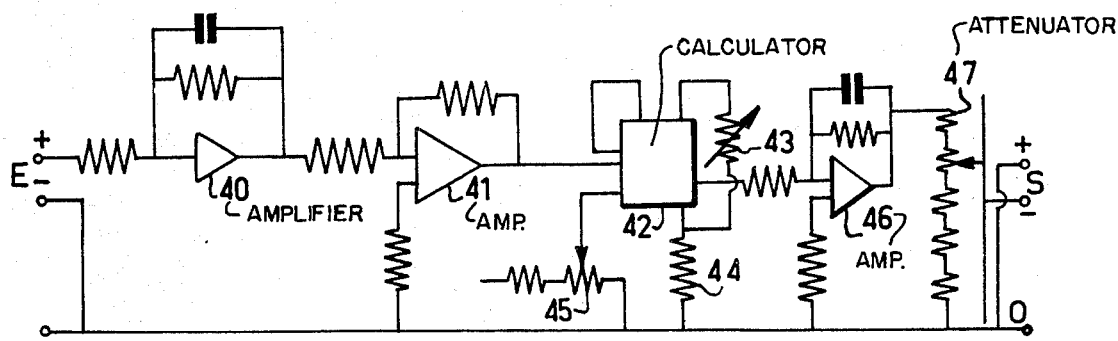
FIG. 3 is a diagram of the device for the linearization of the voltage supplied by the electrometer.

Now refer to FIG. 3.

The voltage at the output $S_2(V_{S_2})$ of the electrometer 13 does not vary linearly as a function of the mass of sulfur detected by the flame photometry detector; it varies in accordance with the law $V_{S2} = K [m]\alpha$; [m] designating the mass of sulfur detected and $\alpha = 1.69$.

There are commercial calculators which furnish an output voltage $V_S$ of the form $V_S = (10/9) V_x(V_y/V_z)^n$, with n constant.

If $V_x$ and $V_z$ are maintained constant (at the values of 0.9 and 10 volts respectively, for instance) one will have $$V_s = K' (V_y)^n.$$

If n is selected such that $n = 1/1.69$ (this can be achieved by means of resistors), one obtains:

$$V_s = k'K [m]^{1.69} \times 1/1.69 = k [m] \quad (1)$$

The circuit which effects this "linearization" of the output voltage of the electrometer is formed of an input E connected to the output $S_2$ of the electrometer 13 (not shown in FIG. 3), an amplifier 40, a voltage inverter consisting of the amplifier 41, calculator 42, with the resistors 43 and 44, and the potentiometer 45, the amplifier 46 and the attenuator 47 connected to the output S, to which the recorder (not shown in FIG. 3) is connected.

The calculator 42 may be a component of type 443.J marketed by the "ANALOG DEVICES" Company.

The resistors 43 and 44 must have a value such that $R_{44}/(R_{44} + R_{43}) = n = 1/1.69$, with $R_{44} + R_{43} \leq 200 \, \Omega$, so that equation (1) is satisfied.

The present invention is furthermore illustrated by the following examples, which are given by way of illustration and not of limitation.

EXAMPLE 1

The device shown in FIGS. 2 and 3 is used to analyze a sample of four sulfur compounds in ethylbenzene. The composition of the sample in sulfur compounds is shown in Table 1 below. The flame ionization detector and its annexes were not used.

The characteristics of the device are as follows:

COLUMN 22: of stainless steel — diameter ⅛ inch (namely 3.18 mm), length 2 meters - stationary phase: "OV 17" at 20% on "Diatoport S" support of 60/80 mesh. The stationary phase is marketed by the Ohio Valley Specialty Chemical Inc.

The column is placed in a thermostatically controlled enclosure, the temperature of which increases linearly, after injection of the sample, by 10° C per minute between 100° and 280° C.

CARRIER GAS: Helium, with a flow rate of 20 cc/minute. VOLUME OF THE SAMPLE INJECTED: 0.5 μ l.

Figure 4:
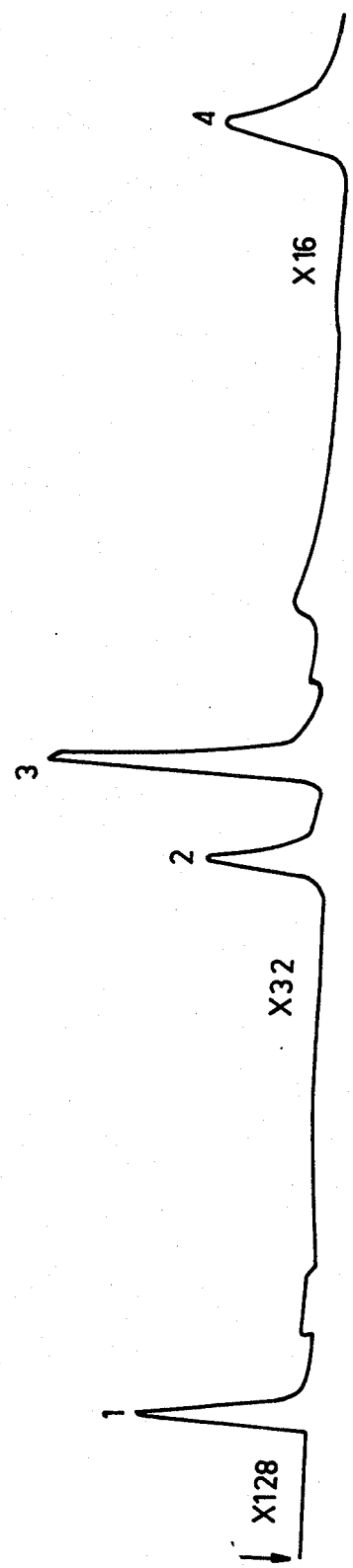
FIG. 4 is the chromatogram obtained by the use of the device according to the invention for the analysis of the sample described in Example I.

FIG. 4 shows the chromatogram obtained by the analysis in accordance with the process of the invention of the sample whose composition is given in the following Table 1.

TABLE 1

| Sulfur COMPOUNDS | Reference peaks in FIG. 4 | CONCENTRATION OF SULFUR | | | |
|---|---|---|---|---|---|
| | | introduced: (in ppm) | determined according to process 1* | | determined according to process 2** |
| | | | (in ppm) | (in units of area) | (in units of area) |
| Thiophene | 1 | 122 | 122 | 5.0 | not determined |
| Ditertbutyl-2,4 thiophene | 2 | 26 | 25 | 1.0 | 1.7 |
| Benzothiophene | 3 | 50 | 52 | 2.1 | 6.7 |

TABLE 1-continued

| | | CONCENTRATION OF SULFUR | | | |
|---|---|---|---|---|---|
| | | | determined according to process 1* | | determined according to process 2** |
| Sulfur COMPOUNDS | Reference peaks in FIG. 4 | introduced: (in ppm) | (in ppm) | (in units of area) | (in units of area) |
| Dibenzothiophene | 4 | 26 | 24.5 | 1.0 | 1.0 |

*Process 1 is the process in accordance with the invention.
**Process 2 is the conventional process using the flame photometry detector, that is to say not comprising prior complete combustion nor signal linearization.

The sensitivity scale of the recording has been indicated in FIG. 4 for each of the peaks. The actual area of the peak is obtained by multiplying the value of the area recorded by the scale.

Table 1 shows the good precision of the analysis effected by means of the device in accordance with the invention. The contents of sulfur compounds are proportional to the areas of the chromatographic peaks. A quantitative determination is therefore possible, which is not true on basis of an analysis effected with the conventional method of use of the flame photometry detector (process 2).

It should furthermore be pointed out that the use of a flame photometry detector makes it possible to avoid interferences with the peak of ethylbenzene, since the latter does not appear on the chromatogram.

EXAMPLE 2

The device shown in FIGS. 2 and 3 is used to analyze a sample formed of a cut coming from a catalytic cracking of a boiling point of between 180° and 280° C.

The characteristics of the device are identical to those described in Example 1, except for the flow of helium, which is 30 cc/minute.

Figure 5:
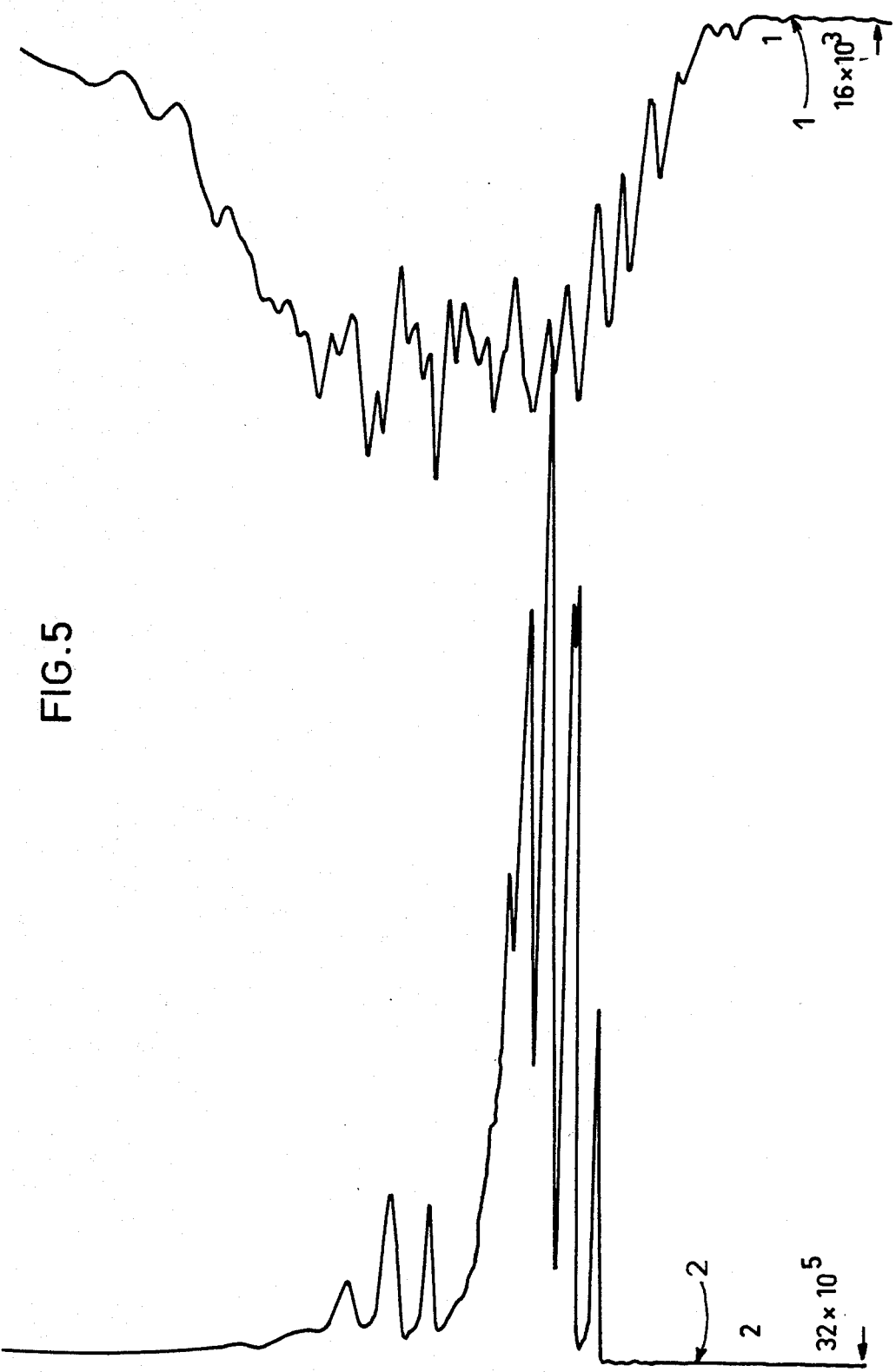
FIG. 5 shows chromatograms obtained with the device of the invention for the analysis of the sample described in Example II.

FIG. 5 shows chromatograms obtained with a double track recorder from a sample of 0.1 $\mu$ l.

The chromatogram marked 1, located on the right of FIG. 5, is the one given by the flame ionization detector located within the combustion enclosure of the sample. It will be noted that the components of the sample are poorly separated and that the interferences between these hydrocarbons and the sulfur compounds are very extensive and make any quantitative determination impossible.

The chromatogram marked 2, located on the left side of FIG. 5, is the one given by the flame photometry detector; the selectivity of this detector permits the elimination of the peaks corresponding to hydrocarbons. The chromatogram is therefore formed exclusively of the sulfur compounds all determined in the form of oxides of sulfur since the sulfur compounds of the sample which were separated by the chromatographic column undergo complete combustion as they are eluted.

The total weight of sulfur in the sample is 2.2%, determined with reference to an outside reference of known concentration, for instance benzothiophene in isoctane, injected in known amount in order to obtain a reference chromatogram.

The scales of the recording of the chromatograms 1 and 2 have been entered in FIG. 5. The points of origin of the recordings have been slightly shifted so as to permit the simultaneous recording of the analysis supplied by the two detectors without risk of collision of the tracing styluses of the double track recorder.

We claim:

1. In a process for the detection of sulfur compounds in a sample, which may contain hydrocarbon compounds, by gas chromatography using a flame photometric detector, the improvement for specific quantitative analysis of a plurality of different sulfur compounds comprising:
   — chromatographic elution of said compounds contained in the sample, thereby separating at least said sulfur compounds;
   — combustion of said eluted compounds to convert completely all of the sulfur in said compounds into sulfur oxides;
   — detecting seriatim the sulfur oxide combustion derivatives of the eluted sulfur compounds with said flame photometric detector and deriving therefrom an output signal which is proportional to the mass of the sulfur in each detected compound raised to a power n, a constant which is characteristic of said sulfur oxides;
   — converting said photometric detector output signal to yield a quantitative linearized signal which is directly proportional to the number of molecules of sulfur detected.

2. A process according to claim 1, further comprising dividing the efflux from said combustion and supplying a predetermined fraction to said flame photometric detector, which fraction is at least small enough to avoid saturation of said detector, so as to give a reliable output signal.

3. A process according to claim 2, wherein $n = 1.69$.

4. A process according to claim 2, further comprising at least a qualitative analysis of said compound with a separate detector at or prior to the combustion but after the chromatographic separation.

5. A process according to claim 4, wherein said separate detector is a flame ionization detector which detects at the combustion of said sample, and wherein said combustion is with hydrogen and an excess of oxygen.

6. A process according to claim 5, further comprising comparatively recording on a time sequence scale the qualitative analysis output from said separate detector and the quantitative linearized signal from the photometric detector.

7. In a device for detecting sulfur compounds in a sample, having in series a flame photometric detector provided with a photomultiplier, an electrometer, and a recorder, and a burner for the combustion of the sample being located upstream of the flame photometric detector, the improvement for specific quantitative detection of said sulfur compounds comprising:
   a leakage bypass means located between said burner and said flame photometric detector for controlling the fraction of efflux from said burner which can pass to said photometric detector;
   — said burner being adapted to ensure the total combustion of said sample;

— linearization means placed in series between the electrometer and the recorder for converting the output voltage of the electrometer into a voltage which is proportional to the number of sulfur molecules detected.

8. A device according to claim 7, further comprising means for feeding the burner continuously with hydrogen and with pure or dilute oxygen, and intermittently with the sample to be analyzed, with an amount of oxygen being in excess.

9. A device according to claim 7, further comprising upstream of the burner, a means for injecting the sample to be analyzed and a column for separation by gaseous phase chromatography of the components of the sample which are diluted in an inert carrier gas.

10. A device according to claim 9, wherein said burner comprises a furnace and an enclosure in which the burner effects the complete combustion of the sample, said enclosure consisting of a tube of refractory material at least part of which is located in said furnace.

11. A device according to claim 7, wherein the electrometer responsive to the flame photometry detector furnishes an output voltage which is proportional to the mass of sulfur detected raised to a power of n and the linearization means comprises a calculator for converting the voltage applied from said electrometer to yield an output voltage from said linearization means which is increased to a power equal to $1/n$.

12. A device according to claim 9, wherein $n = 1.69$.

13. A device according to claim 10, wherein said linearization means to linearize the output voltage of the electrometer comprises a first amplifier, an inverter connected to receive an output signal from said amplifier, said calculator connected to said inverter, a second amplifier connected to receive an output signal from said calculator, and an attenuator to control the amplitude of the output signal of said second amplifier.

14. A device according to claim 12, further comprising a separate detection means arranged downstream of the chromatographic separation column and at or upstream of said burner, for at least qualitative analysis of the components of said sample.

15. A device according to claim 14, wherein said separate detection means is a flame ionization detector placed at said burner.

* * * * *